(12) United States Patent
Ripoche et al.

(10) Patent No.: US 10,470,726 B2
(45) Date of Patent: Nov. 12, 2019

(54) METHOD AND APPARATUS FOR X-RAY SCAN OF OCCLUSAL DENTAL CASTS

(71) Applicant: TROPHY, Croissy Beaubourg (FR)

(72) Inventors: Xavier Ripoche, Mandres les Roses (FR); Delphine Reynard, Montreuil (FR); Pascal Narcisse, Boulogne Billancourt (FR); Gael Roberts, Vincennes (FR)

(73) Assignee: TROPHY, Croissy Beaubourg (FR)

( * ) Notice: Subject to any disclaimer, the term of this patent is extended or adjusted under 35 U.S.C. 154(b) by 0 days.

(21) Appl. No.: 15/573,585

(22) PCT Filed: May 15, 2015

(86) PCT No.: PCT/IB2015/001558
§ 371 (c)(1),
(2) Date: Nov. 13, 2017

(87) PCT Pub. No.: WO2016/184246
PCT Pub. Date: Nov. 24, 2016

(65) Prior Publication Data
US 2018/0146934 A1    May 31, 2018

(51) Int. Cl.
*A61B 6/14*    (2006.01)
*G06T 17/20*    (2006.01)
(Continued)

(52) U.S. Cl.
CPC ............... *A61B 6/14* (2013.01); *A61B 6/032* (2013.01); *A61B 6/4085* (2013.01); *A61B 6/466* (2013.01);
(Continued)

(58) Field of Classification Search
CPC ......... A61B 6/14; A61B 6/032; A61B 6/4085; A61B 6/466; A61B 6/5205; A61B 6/4441;
(Continued)

(56) References Cited

U.S. PATENT DOCUMENTS 6,579,095 B2    6/2003    Marshall et al.
7,347,690 B2    3/2008    Jordan et al.
(Continued)

FOREIGN PATENT DOCUMENTS

WO    WO 2014060595    4/2014

OTHER PUBLICATIONS

Vatech Co., Ltd. "Vatech EzSensor 1.5", Sep. 2014. pp. 1-3. https://www.amazon.com/Vatech-EZ-Sensor-EzSensor-EZSENSOR15/dp/B00MPV1RZY.*

(Continued)

*Primary Examiner* — Chong Wu

(57) ABSTRACT

An extra-oral imaging apparatus can obtain a 3D volume image of a portion of a head of a patient. Exemplary dental apparatus and/or method embodiments can provide 3D mesh models of surfaces of the maxillary dental arch and the mandibular dental arch in a 3D volume image obtained from a single extraoral scan of physical casts of the maxillary dental arch and the mandibular dental arch in an occlusal relationship. In one exemplary embodiment, a first 3D mesh model of surfaces of the maxillary dental arch model and a second 3D mesh model of surfaces of the mandibular dental arch model are generated. Then, contact areas where the first 3D mesh model and the second 3D mesh model intersect are removed to separate the first and second mesh models. In another exemplary embodiment, the first 3D mesh model and the second 3D mesh model can be aligned.

15 Claims, 12 Drawing Sheets

(51) Int. Cl.
*G06T 19/20* (2011.01)
*A61B 6/00* (2006.01)
*A61B 6/03* (2006.01)
*A61C 7/00* (2006.01)
*A61C 19/05* (2006.01)
*G01N 23/046* (2018.01)
*G06T 15/30* (2011.01)
*A61C 9/00* (2006.01)
*A61C 13/00* (2006.01)

(52) U.S. Cl.
CPC ............ *A61B 6/5205* (2013.01); *A61C 7/002* (2013.01); *A61C 9/004* (2013.01); *A61C 13/0004* (2013.01); *A61C 19/05* (2013.01); *G01N 23/046* (2013.01); *G06T 15/30* (2013.01); *G06T 17/20* (2013.01); *G06T 19/20* (2013.01); *A61B 6/4441* (2013.01); *G01N 2223/6123* (2013.01); *G06T 2210/21* (2013.01); *G06T 2210/41* (2013.01); *G06T 2219/2004* (2013.01)

(58) Field of Classification Search
CPC ..... A61C 7/002; A61C 9/004; A61C 13/0004; A61C 19/05; G01N 23/046; G01N 2223/6123; G06T 15/30; G06T 17/20; G06T 19/20
See application file for complete search history.

(56) References Cited

U.S. PATENT DOCUMENTS

| | | | |
|---|---|---|---|
| 7,349,130 | B2 | 3/2008 | Vadnais et al. |
| 2002/0150859 | A1 | 10/2002 | Imgrund |
| 2012/0236135 | A1 | 9/2012 | Daniel et al. |
| 2013/0249893 | A1 | 9/2013 | Mehra |
| 2013/0308846 | A1* | 11/2013 | Chen ................ G06T 7/0012 382/131 |
| 2016/0148370 | A1* | 5/2016 | Maury ................ A61C 9/0006 348/77 |

OTHER PUBLICATIONS

PCT, International Search Report, International Application No. PCT/162015/001558, 3 pages, dated Mar. 9, 2016.
PCT, Written Opinion of the International Searching Authority, International Application No. PCT/IB2015/001558, 7 pages, dated Mar. 9, 2016.
Japanese Office Action from JP Application No. 2017-559554 dated Jan. 8, 2019, pp. 1-7.

* cited by examiner

METHOD AND APPARATUS FOR X-RAY SCAN OF OCCLUSAL DENTAL CASTS

FIELD OF THE INVENTION

The invention relates generally to the field of dental x-ray imaging, and more particularly, to apparatus and methods for obtaining volumetric images of teeth. Further, the invention relates to an occlusal dental imaging apparatus and/or methods.

BACKGROUND

Radiological imaging is acknowledged to be of value for the dental practitioner, helping to identify various problems and to validate other measurements and observations related to the patient's teeth and supporting structures. Among x-ray systems with particular promise for improving dental care is the extra-oral imaging apparatus that is capable of obtaining one or more radiographic images in series and, where multiple images of the patient are acquired at different angles, combining these images to obtain a 3-D reconstruction showing the dentition of the jaw and other facial features for a patient. Various types of imaging apparatus have been proposed for providing volume image content of this type. In these types of systems, a radiation source and an imaging detector, maintained at a known distance (e.g., fixed or varying) from each other, synchronously revolve about the patient over a range of angles, taking a series of images by directing and detecting radiation that is directed through the patient at different angles of revolution. For example, a volume image (e.g., reconstruction of 3D or volume images) that shows the shape and dimensions of the head and jaws structure can be obtained using computed tomography (CT), such as cone-beam computed tomography (CBCT), or other volume imaging method. The resulting volume images are acknowledged to be of particular value for obtaining useful information for assisting diagnosis and treatment.

Before an orthodontic treatment, it is current practice to create a virtual 3D model of the upper and lower patient's jaw. The virtual teeth are then segmented and can be displaced relative to each other to simulate an orthodontic treatment plan. More than one technique can be used to acquire a 3D model of teeth. First the patient's mouth can be scanned using an intra oral camera that acquires a plurality of frames before reconstructing the 3D model. Positive physical casts representing the patient's lower and upper jaw can also be scanned by the intra oral camera. Alternatively, the two positive physical casts representative of the mandible and the maxillary of the patient can be separately scanned using a CBCT x-ray device. A CBCT device can include a gantry supporting an X-ray source and a sensor opposing each other that rotates about a plaster scan positioned a support. A plurality of 2D frames is acquired by the sensor during the rotation. A 3D matrix of grey levels is reconstructed using some standard algorithms.

A crucial point is to register the lower and the upper jaw virtual models in actual occlusion conditions. Indeed, obtaining a good occlusion registration of the upper and the lower teeth models is one necessary condition for a good assessment of the initial conditions of the patient teeth before starting an orthodontic treatment.

It can be appreciated that there is still a need for dental x-ray imaging apparatus and/or methods that can provide a cheaper, rapid, and/or accurate assessment of initial conditions including occlusion registration of the upper and the lower teeth of a patient.

SUMMARY

An aspect of this application is to advance the art of medical digital radiography, particularly for dental applications.

Another aspect of this application is to address, in whole or in part, at least the foregoing and other deficiencies in the related art.

It is another aspect of this application to provide, in whole or in part, at least the advantages described herein.

An advantage provided by apparatus and/or method embodiments of the application relates to providing occlusion registration of the upper and the lower teeth virtual models using casts of upper and lower teeth of a patient arranged and scanned in actual occlusion conditions.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the disclosure, there is provided a method, executed at least in part on data processing hardware, that can include 3-dimensionally x-ray scanning the physical positive models of the dental arches while the physical positive models of the dental arches are in an occlusal relationship to obtain 3-D image data including data representing each of the dental arch physical positive models; constructing 3-D models including a maxillary dental arch representation and a mandibular dental arch representation aligned in an occlusal arrangement using the 3-D image data; and displaying, transmitting or storing the 3-D model including the maxillary dental arch representation and the mandibular dental arch representation aligned in the occlusal arrangement.

According to another aspect of the disclosure, there is provided a method for constructing a 3-D model incorporating 3-D scan image data of a maxillary dental arch positive physical model and of an opposing mandibular dental arch positive physical model that can include 3-dimensionally x-ray scanning the positive physical models of the dental arches while the positive physical models of the dental arches are in an occlusal relationship to obtain 3-D image data including data representing each of the dental arch positive physical models; constructing 3-D models including a maxillary dental arch representation over a mandibular dental arch representation; generating a first 3D mesh model of surfaces of the maxillary dental arch representation and a second 3D mesh model of surfaces of the mandibular dental arch representation; determining contact areas where the first 3D mesh model and the second 3D mesh model intersect; identifying transition zones of the contact areas where the first 3D mesh model and the second 3D mesh model intersect; clipping the contact areas using information of the transition zones to separate and close the first 3D mesh model and the second 3D mesh model; and displaying, transmitting or storing the closed first 3D mesh model and the closed second 3D mesh model.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting x-ray system components, for example, are not shown in the drawings in order to simplify description.

DESCRIPTION OF EXEMPLARY EMBODIMENTS

Figure 1:
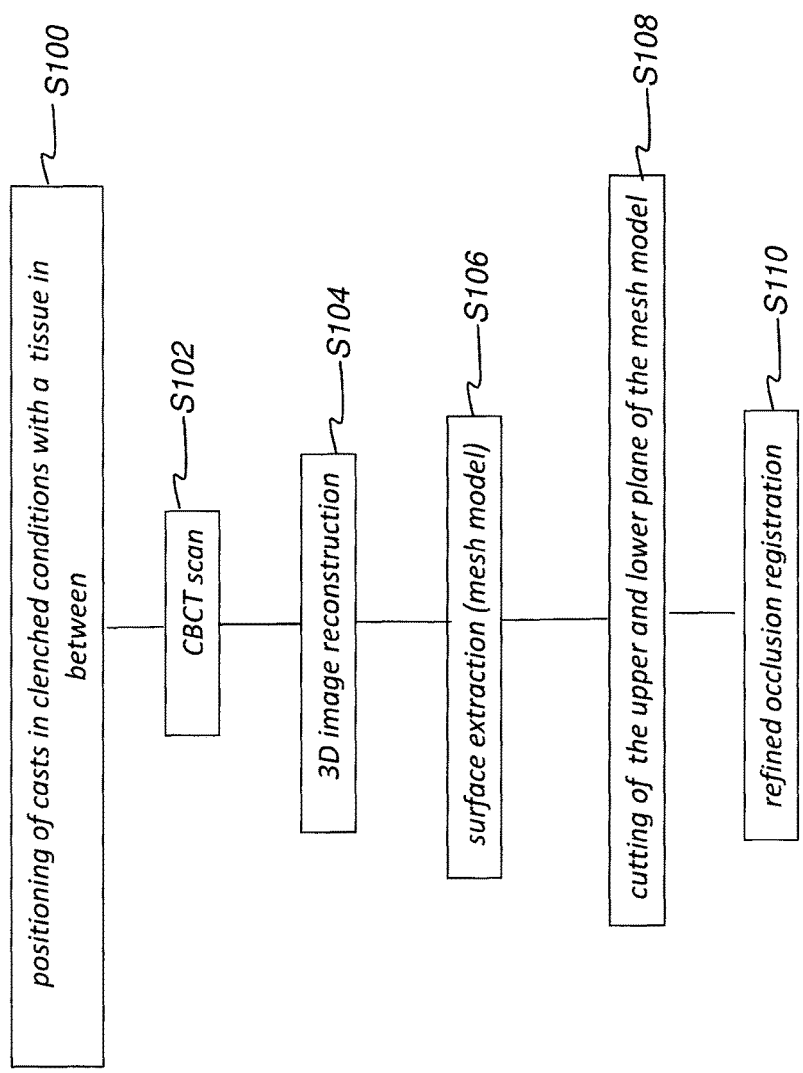
FIG. 1 is a flowchart that shows an exemplary method embodiment according to the application.

The following is a description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional or volume images and a pixel for 2-dimensional (2-D) images. Volume images, such as those from CT or CBCT apparatus, are formed by obtaining multiple 2-D images of pixels, taken at different relative angles, then combining the image data to form corresponding 3-D voxels. For the purposes of the description herein, the terms voxel and pixel can generally be considered equivalent, describing an image elemental datum that is capable of having a range of numerical values. Voxels and pixels have attributes of both spatial location and image data code value.

In the context of the present disclosure, the term "code value" refers to the value that is associated with each volume image data element or voxel in the reconstructed 3-D volume image. The code values for CT images are often, but not always, expressed in Hounsfield units (HU).

Apparatus and/or method embodiments according to the application aim at providing a cheaper, rapid, and/or accurate assessment of orthodontic conditions including occlusion registration of the upper and the lower teeth using casts of upper and lower teeth of a patient. A crucial point is to register the lower and the upper virtual models in actual occlusion conditions.

Again a starting point is to register the lower and the upper virtual models in actual occlusion conditions. According to the related art, a lower cast, an upper cast, and a wax bite (corresponding to the occlusal conditions) of the patient's teeth with teeth imprint on both sides are scanned. Then, three virtual 3D models of the lower teeth, the upper teeth and the wax bite model are reconstructed. The virtual teeth of a virtual lower teeth model are registered with the virtual prints of the lower face of the virtual wax bite model, and the virtual teeth of the upper teeth model are registered with the virtual prints on the upper face of the virtual teeth of the upper teeth model. Then, the upper teeth model is registered to the lower teeth model. The registration of the upper and lower teeth models is made possible by the creation of the third virtual model, the virtual model of the wax bite, acting as a go-between in the registration process. See for example, U.S. Pat. Nos. 7,347,690 and 7,349,130. However, there remains a need to make the process less cumbersome and/or more accurate by decreasing the number of necessary virtual models.

According to the alternative related art, the physical casts representing the lower and the upper jaws are positioned side by side on a support. Here, the upper jaw physical cast includes a polygonal base that supports the physical model of the patient's jaw. Also, the lower jaw physical cast includes a polygonal base that supports the physical model of the patient's jaw. The rear face of each of the physical polygonal bases is cut in such a way that the two rear faces are aligned when the casts are in actual occlusion. Therefore, once virtual models of both the upper jaw and lower jaw physical casts are reconstructed, the alignment of both virtual rear faces of the polygonal bases defines the registration of the upper and lower teeth models in actual occlusal conditions. This related art registration method necessitates the use of landmarks, namely the rear faces, to obtain the registration of both virtual jaw models. See for example, U.S. Pat. No. 6,579,095. However, there remains a need to simplify and/or increase accuracy of the registration process by suppressing the step of registration of landmarks such as the rear faces of a virtual model.

In exemplary registration processes according to method and/or apparatus embodiments of this application, both upper jaw and lower jaw physical casts can be scanned together in actual occlusion conditions (e.g., using a CBCT device). Advantages to method and/or apparatus embodiments of this application include that one single scan is necessary, increase registration accuracy and/or no registration of landmarks is needed. Additional advantages include that the reconstructed models are already very close to a desired position or maximum intercuspation position because the scanned physical models (casts) were already in occlusion condition. Such situations are not encountered in the methods of the related art in which features like the rear faces of the base are registered or in which a third component is used. However, in this case opposite teeth of the upper and the lower physical models are in an actual occlusal condition or clenched at the time of the CBCT scan and consequently the upper and lower reconstructed virtual model are merged. It is then difficult, time consuming and/or complicated to separate both upper and lower reconstructed virtual models. Method and/or apparatus embodiments of this application address or overcome such disadvantages.

Referring to FIG. 1, a flow chart that shows an exemplary method of occlusion registration of the upper and the lower teeth virtual models using physical casts of upper and lower teeth of a patient according to embodiments of the application will now be described. The method can be applied to dental imaging apparatus/x-ray systems shown in FIG. 12; however, the method of FIG. 1 is not intended to be limited thereby.

Figure 2:
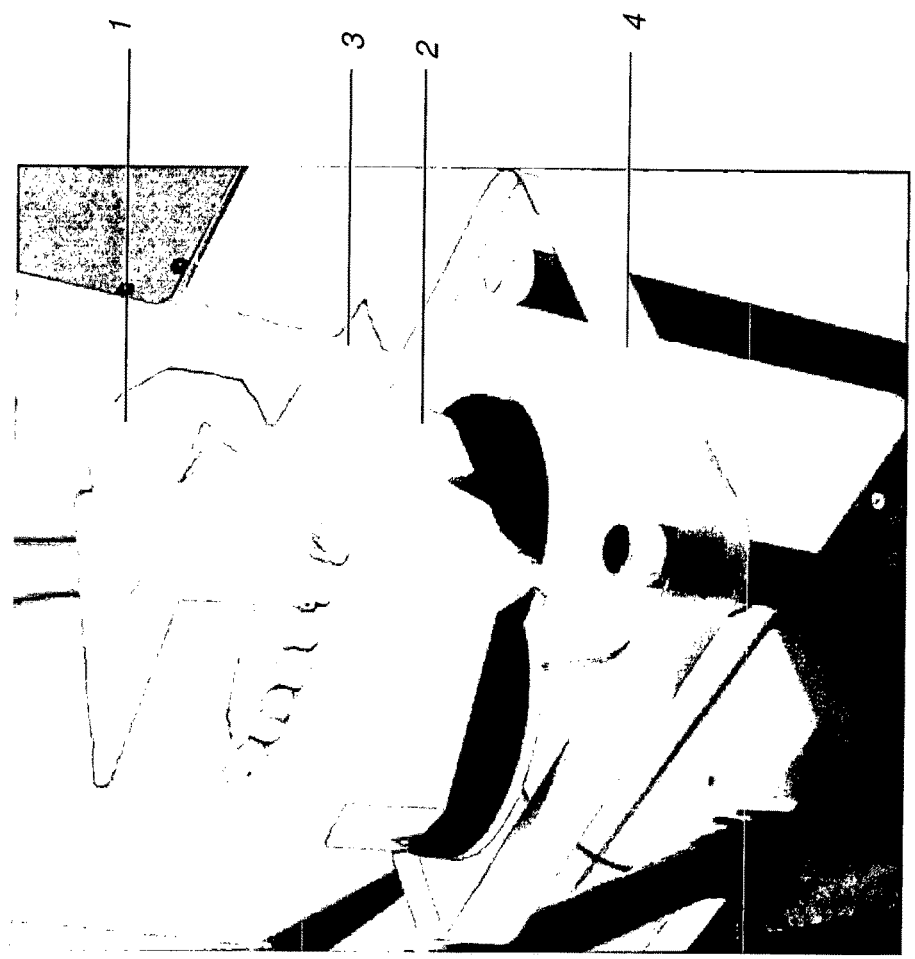
FIG. 2 is a diagram that shows a perspective view of an upper jaw positive physical cast and a lower jaw positive physical cast in actual occlusion conditions at a CBCT device with a thin intermediary.
Figure 3:
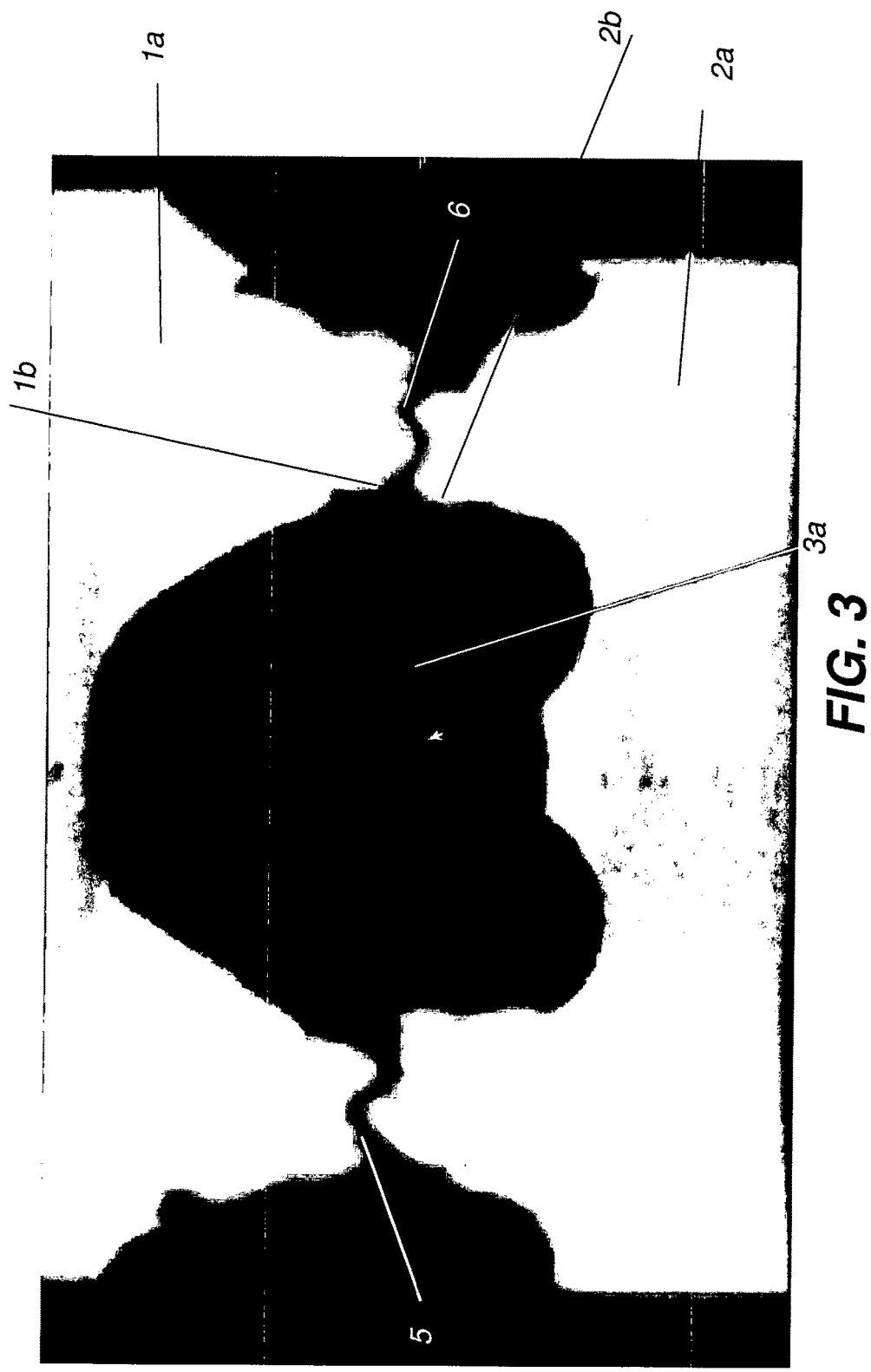
FIG. 3 is a diagram that shows a cross sectional view of a 3D reconstruction of a CBCT scan of stacked jaw casts and a thin conformal intermediary.

Initially, as shown in FIG. 1, the upper cast 1 and the lower 2 casts are positioned in actual occlusion conditions on a support 4 of a CBCT device (not shown) with a thin conformal intermediary interface between them (step 100). FIG. 2 is a diagram that shows a perspective view of the upper cast 1 and the lower 2 casts in actual occlusion conditions at a CBCT device with a tissue 3 in between. In exemplary embodiments, the tissue 3 can be almost transparent to x-ray and can have a thickness of a few millimeters, typically between 1 and 5 millimeters. A CBCT scan of the three stacked objects can then be carried out (step 102), and then a three dimensional matrix of grey levels composed of voxels is reconstructed (step 104). FIG. 3 is a diagram that shows a cross sectional view of a 3D reconstruction of a scan of stacked upper and lower jaw casts and a thin conformal (e.g., not rigid) intermediary. As shown in FIG. 3, a 3D image 3a of the tissue 3 can be distinguished between both a 3D image 1a of the upper cast 1 and a 3D image 2a of the lower cast 2 on the cross sectional view of the reconstruction from the CBCT scan. Advantageously, the 3D images 1a and 2a of the casts are separated by gaps such as gap 5 and gap 6 as the scanned physical casts 1, 2 were not in contact.

Polygonal 3D mesh data of surfaces 1b and 2b of the images 1a and 2a of the cast 1 and 2 can then be extracted using standard commercially methods (step 106) such as available Marching Cubes algorithms. Advantageously, because the images 1a and 1b do not contact, two separate 3D mesh models of the upper jaw and lower jaw surfaces are obtained and no further step is necessary to segment the two 3D mesh models. In a successive, preferably automatic process, the upper and lower plane surface of the upper mesh model and the lower mesh model respectively can be cut to trim the parts of the mesh models remote or opposite from the relevant teeth surface 1b and 2b information (step 108).

At this point, the two surface mesh models are extracted in good occlusal conditions or occlusal relationship. However, an optional step can be added to the method embodiments shown in FIG. 1 that includes a refined occlusion adjustment (step 110). In the optional refined occlusion adjustment step, the two surface mesh models are virtually moved until they collide in an increased amount or toward their maximum intercuspation position. In one embodiment, the refined occlusion adjustment step is done using an algorithm that can automatically increase and preferably maximizes a number of contact points between the two surface mesh models. For example, a first contact point is found using a Z translation; and the first contact point is used as the fulcrum of a new transformation to find other contact points. As the initial position of the two surface mesh models is really near the wanted or maximum intercuspation position, this geometrical transformation can generally be less than 1 mm in x, y, z directions (e.g., three orthogonal directions) and angle less than 5° (e.g., angle of rotation between models). In one embodiment, the Z transformation can result in two or more "first" contact points, which can then be used together in subsequent transformations. In another embodiment, the Z transformation is not the first transformation in the series of transformations.

At this point, the voxel models are accurately registered. After a teeth segmentation step (not shown) for each of the registered upper and lower jaw models, a virtual orthodontic treatment plan can be determined and/or simulated.

Figure 4:
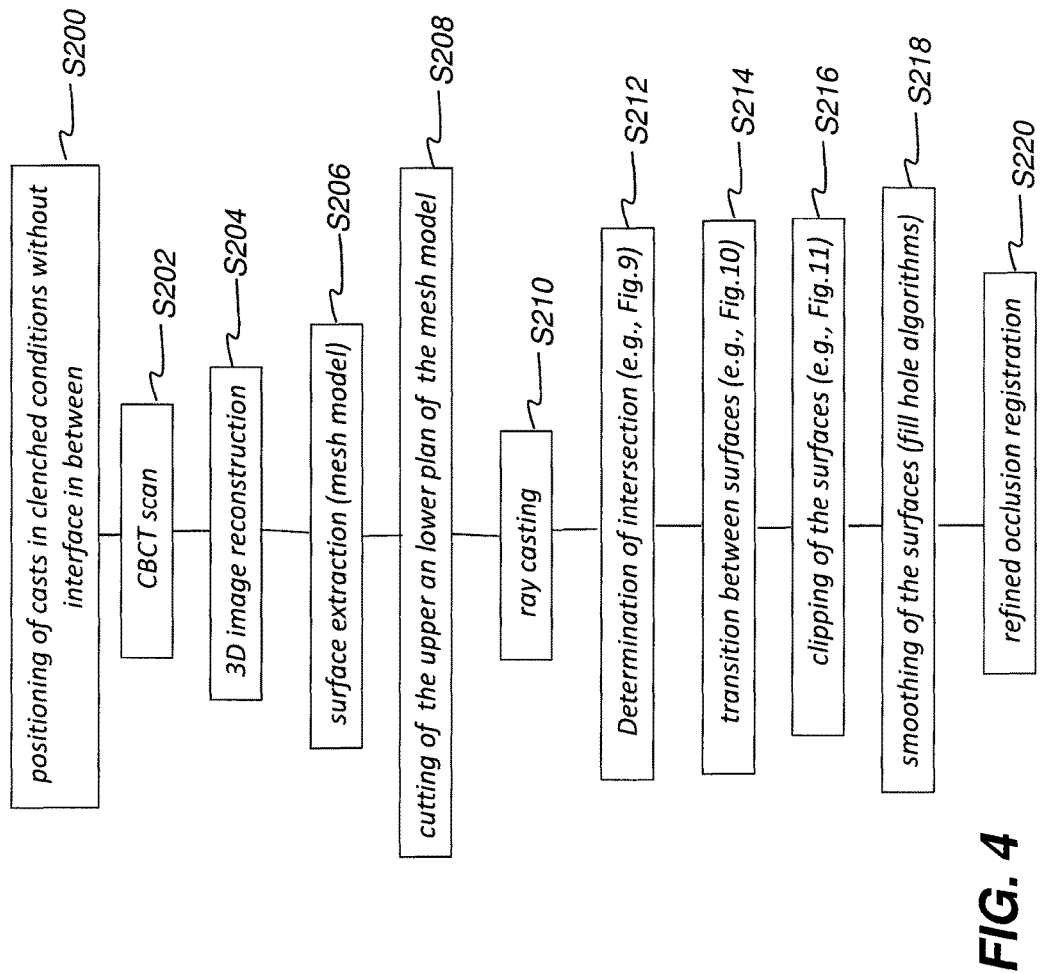
FIG. 4 is a flowchart that shows another exemplary method embodiment according to the application.

Referring to FIG. 4, a flow chart that shows an exemplary method of occlusion registration of upper and lower teeth virtual models using physical casts of upper and lower teeth of a patient according to embodiments of the application will now be described. The method can be applied to dental imaging apparatus/x-ray systems shown in FIG. 12; however, the method of FIG. 4 is not intended to be limited thereby.

As shown in FIG. 4, first the upper cast 1 and the lower cast 2 are positioned directly adjacent to each other in actual occlusion conditions on a support 4 of a CBCT device (step 200). Thus, in step 200, the upper cast 1 and the lower 2 cast are positioned directly in contact with each other in actual occlusion conditions on the support 4 of a CBCT device without any added interface or intermediary therebetween.

The steps 202, 204, 206 and 208 are similar to the steps 102, 104, 106 and 108 of the first method. Accordingly, a detailed description of processes at steps 202, 204, 206 and 208 will not be repeated here. Briefly, A CBCT scan of the two stacked objects can then be carried out (step 202), and then a three dimensional matrix of grey levels composed of voxels is reconstructed (step 204). Polygonal 3D mesh data of surfaces 1b and 2b of the images 1a and 2a of the cast 1 and 2 can then be extracted using known commercially methods (step 206). In a successive, preferably automatic process, the upper and lower plane surface of the upper mesh model and the lower mesh model respectively can be cut to trim the parts of the mesh models remote or opposite from the relevant teeth surface 1b and 2b information (step 208).

Figure 5:
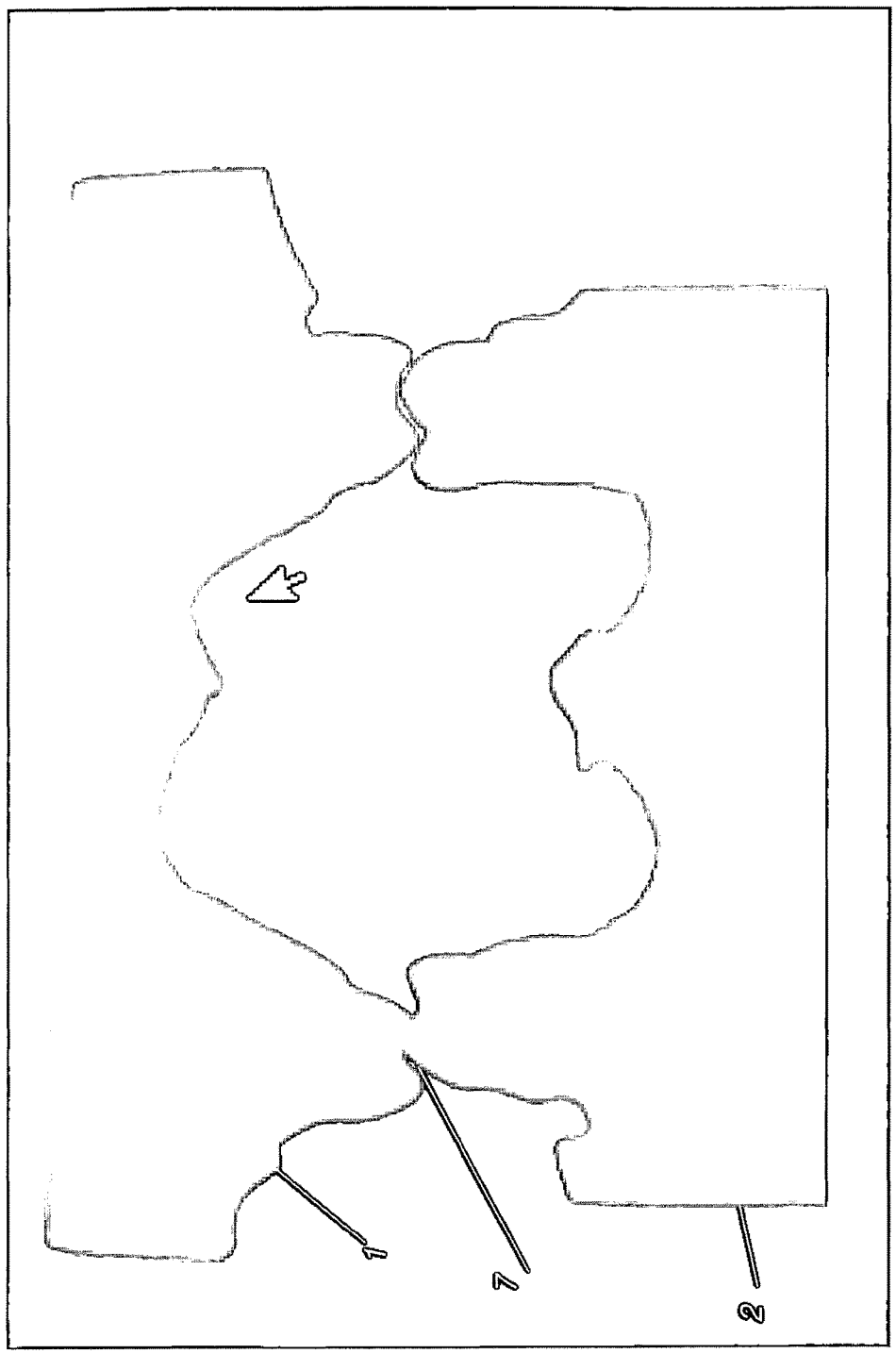
FIG. 5 is a diagram that shows a cross sectional view of a 3D image (or 3D grey level matrix) representing the upper jaw cast and lower jaw cast in occlusion.
Figure 6:
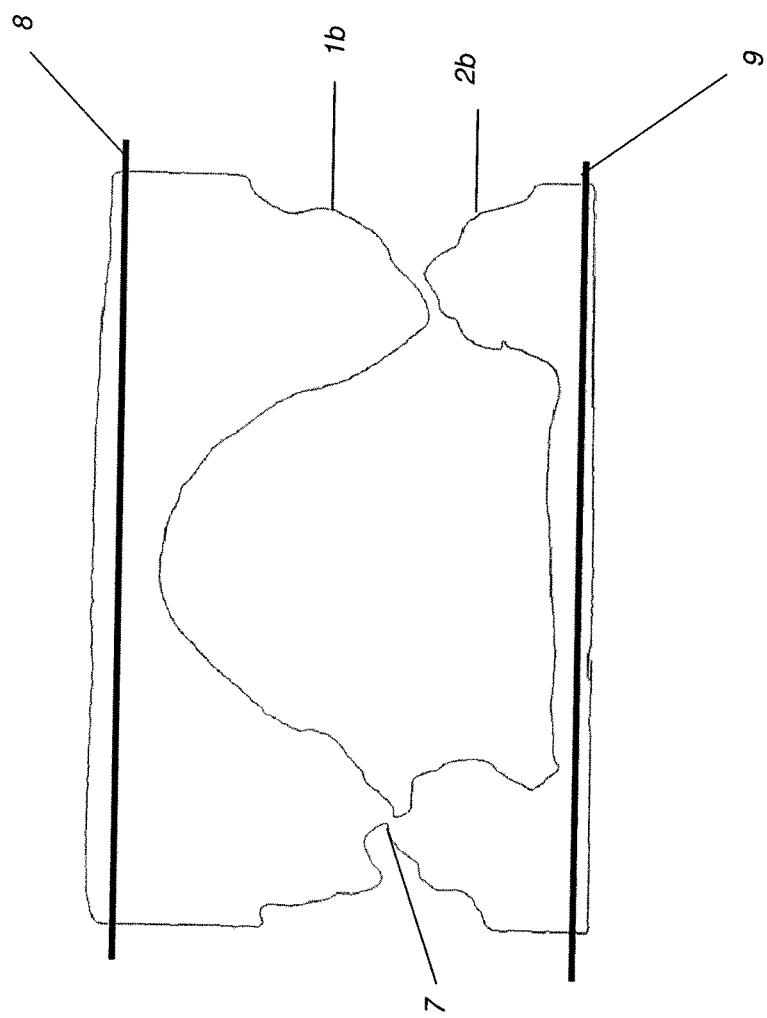
FIG. 6 is a diagram that show two different portions (above a first bounding plane and below a second bounding plane) of the 3D image of the upper jaw cast and lower jaw cast in occlusion that are removed from the upper and lower borders of the 3D image.
Figure 7:
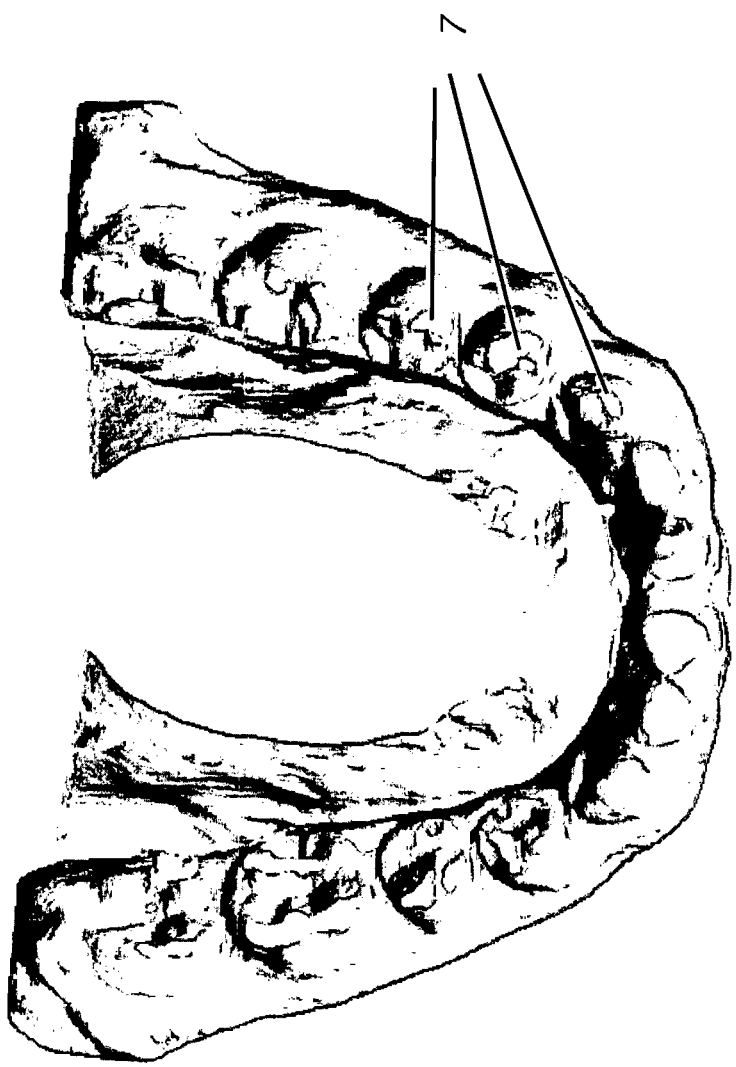
FIG. 7 is a diagram that shows a top view of one 3D surface of the lower jaw cast with holes representing area of contact with the upper jaw cast.

FIG. 5 is a diagram that represents the 3D image (or 3D grey level matrix) representing the upper cast 1 and lower cast 2 in occlusion (e.g., without anything between them). As shown in FIG. 5, there appears to exist a contact region 7 between the upper jaw 3D image and the lower jaw 3D image. The contact region 7 can be highlighted in the voxel model (obtained from the surface extraction step 206). FIG. 7 represents a top view of one surface 1b of the lower cast 1 with holes representing areas of contact such as contact areas 7 between the upper jaw 3D image and the lower jaw 3D image. Such contact areas are clearly an impediment to the separation of the upper and lower virtual voxel-based surfaces. FIG. 6 is a diagram that shows a cross sectional view of the 3D image of upper jaw cast and lower jaw cast in occlusion showing two different portions (above a first bounding plane and below a second bounding plane) of the 3D image that are removed from the upper and lower borders of the 3D image. As previously described (e.g., step 108), the removal of the lower and upper plane surface (step 208) is done using two planes 8 and 9 that can preferably be parallel to the occlusal plane and preferably positioned (e.g., typically at 5 mm) from the upper and lower borders of the 3D image as shown in FIG. 6. The parts of the surfaces 1a and 1b that are on the outer side of the two planes 8 and 9 shown in the 3D image are removed (e.g., from further image processing).

Figure 8:
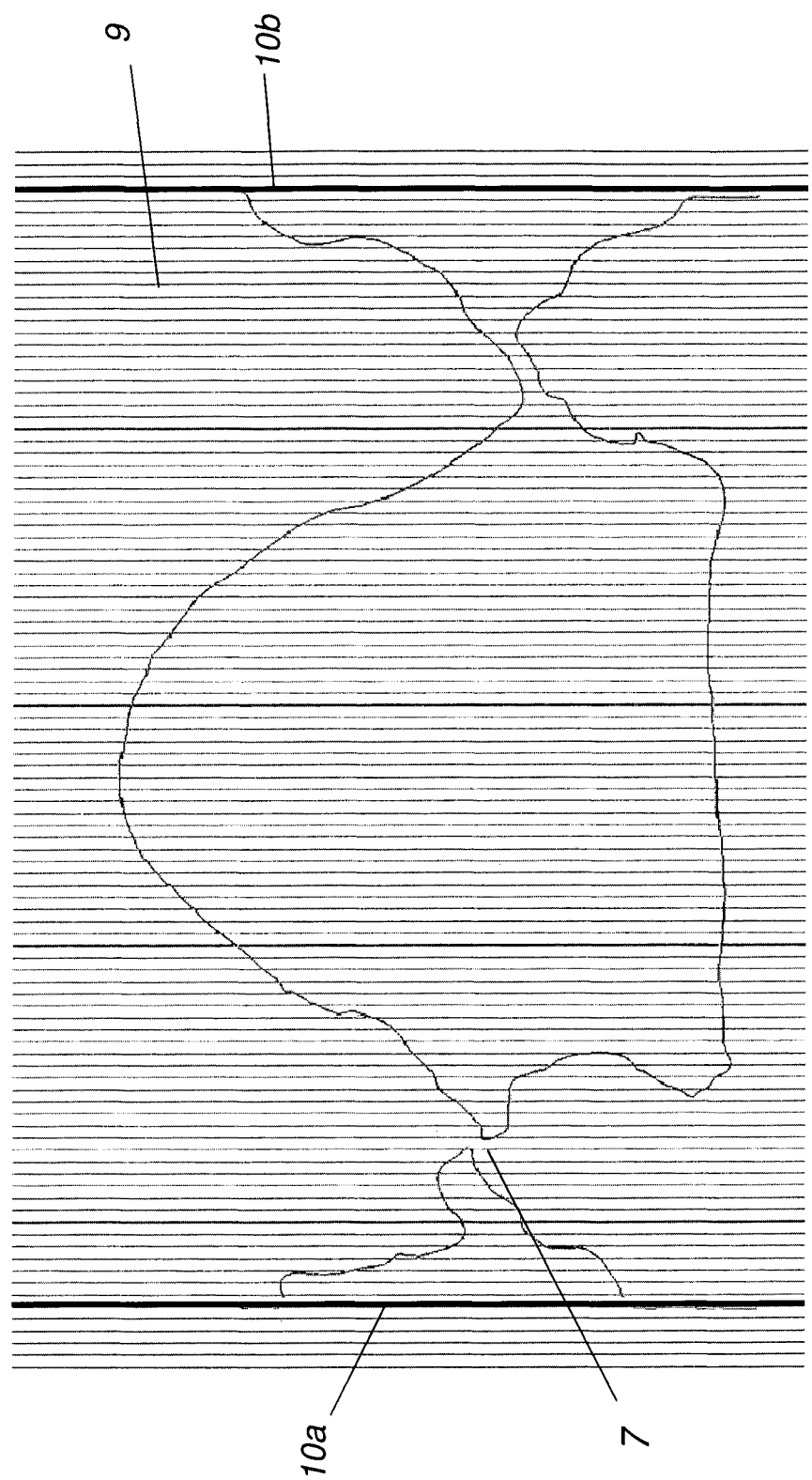
FIG. 8 is a diagram that shows a cross sectional view of a grid of rays that cross a 3D occlusal jaw model orthogonally to an occlusal plane.

The process then advances to simulate a grid of rays 9 (e.g., launched from the top of the model) that cross the model orthogonally to the occlusal plane of the voxel-based models (step 210). FIG. 8 is a diagram that shows a cross sectional view or 2D slice of a grid of rays that cross the model orthogonally to the occlusal plane. Preferably, only rays 9 that pass inside the feature edge, namely between two border lines 10a and 10b defined on each slice, are considered. Rays 9 outside the border lines 10a and 10b can be removed.

Figure 9:
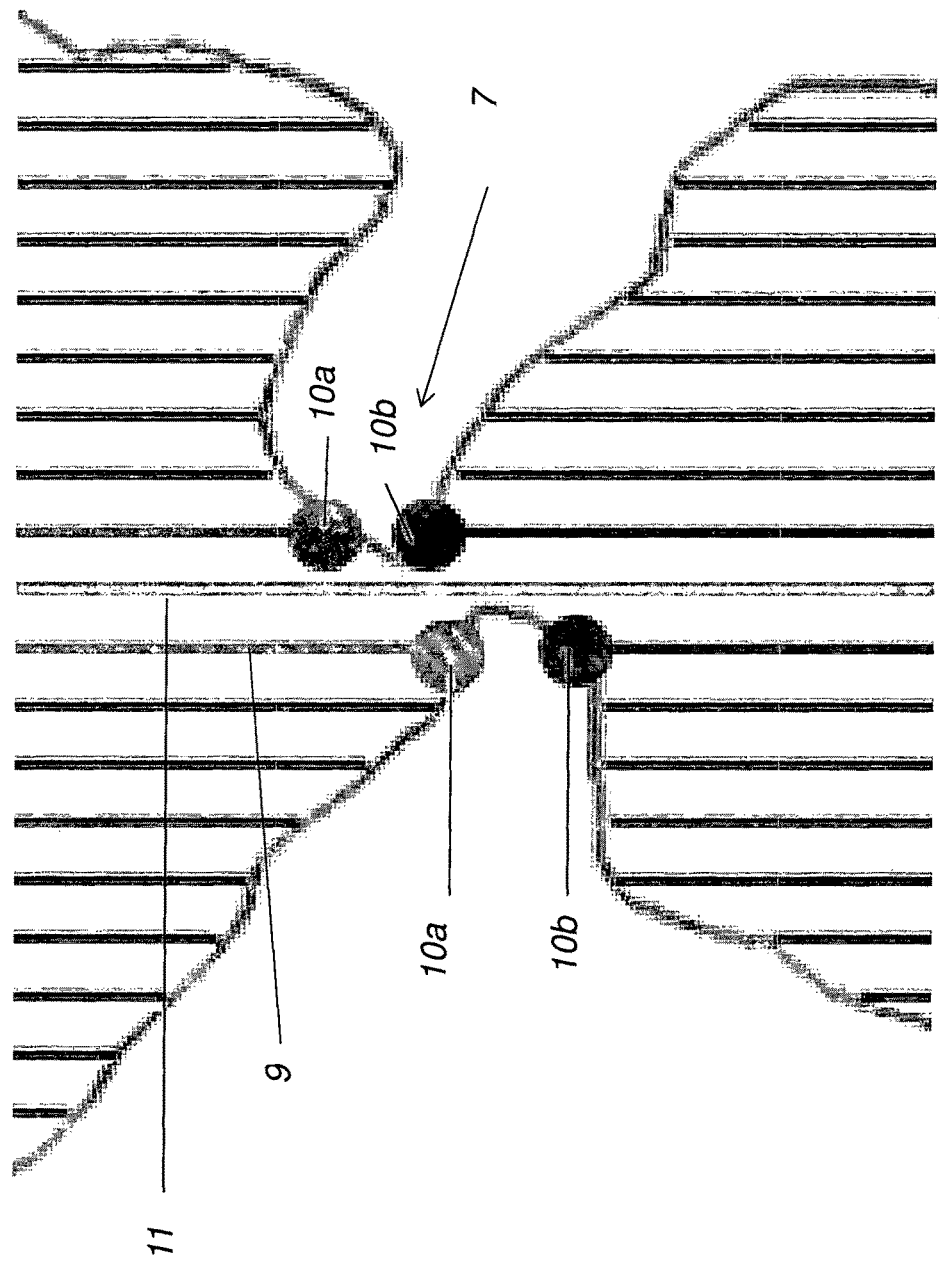
FIG. 9 is a diagram that shows a cross sectional view of intersections of the orthogonal rays with the 3D maxillary and mandibular tooth surfaces.

The process then advances to the determination of the intersections of the rays with the maxillary surfaces 1b and mandibular surfaces 2b (step 212). FIG. 9 is a diagram that shows a cross sectional view of intersections of the orthogonal rays with the 3D maxillary and mandibular tooth surfaces. Except for or out of contact areas 7, rays 9 intersect the maxillary surface 1a at a point 10a and the mandibular surface 1b at the point 10b. As shown in FIG. 9, at a position corresponding to a contact area 7, the ray 11 does not intersect the voxel-based surface 1a or 1b. This step 212 can allow the localization of the contact area 7.

Figure 10:
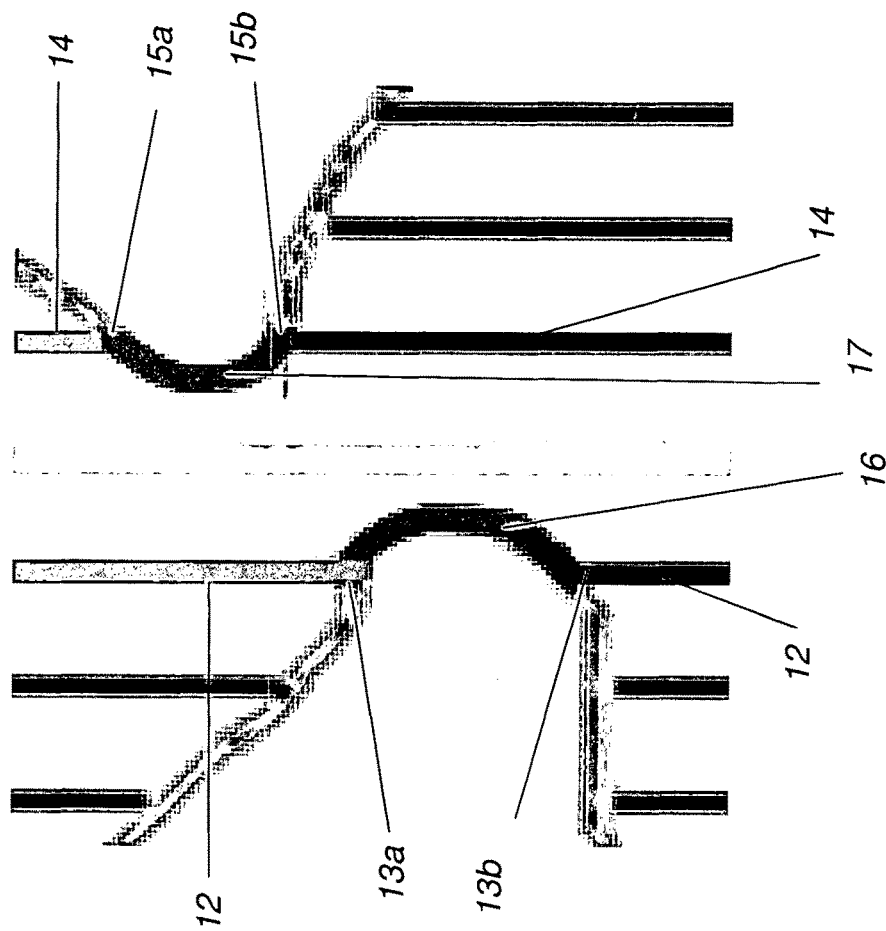
FIG. 10 is a diagram that shows a cross sectional view of transition zones of contact areas of the 3D maxillary and mandibular tooth surfaces.

The process then advances to the identification of transition zones of contact areas like the contact area 7 (step 214). For example in step 214, rays 12 and 14 intersecting the maxillary surfaces 1a and the mandibular surfaces 1b that are located at the closest position of the contact area 7 are identified as well as the two pairs of intersection points 13a, 13b and 15a, 15b. FIG. 10 is a diagram that shows a cross sectional view of transition zones of contact areas of the 3D maxillary and mandibular tooth surfaces. As shown in FIG. 10, the zones that lie between the points of each pair of points on both sides of the contact area can be identified as the transition zones. A transition zone 16 is the area between the intersection points 13a and 13b and a transition zone 17 is the area between the intersection points 15a and 15b.

Figure 11:
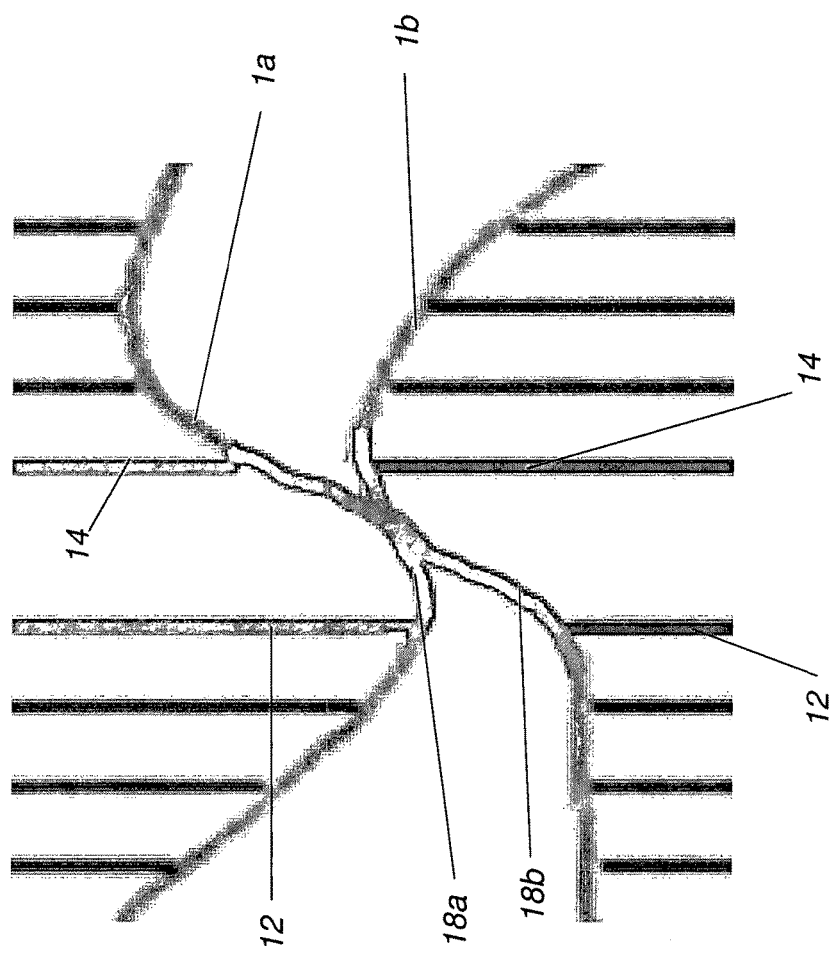
FIG. 11 is a diagram that shows a cross sectional view of closed 3D maxillary and mandibular tooth surfaces after clipping of the transition zones according to embodiments of the application.

Then, clipping of both surfaces 1a and 1b at the position of the contacts area 7 can then be performed using information of the transition zones (step 216). In one embodiment, the clipping of both surfaces 1a and 1b at the position of the contacts area 7 is carried out by an algorithm that uses the curvature information (e.g., maximum curvature information) of the transition zone. Two closed surfaces 1a and 1b can now be obtained with new segments 18a and 18b replacing the initial segments 16 and 17 of the contact area. FIG. 11 is a diagram that shows a cross sectional view of closed 3D maxillary and mandibular tooth surfaces after clipping of the transition zones according to embodiments of the application.

Once the 3D maxillary and mandibular tooth surfaces are separated, the process then advances to smooth the closed 3D maxillary and mandibular tooth surfaces (step 218). In one embodiment, a standard fill hole algorithm known from the art can be applied to get smooth or smoother closed 3D maxillary and mandibular tooth surfaces. Optionally, an additional process for a refined occlusion registration (step 220) similar to processes of step 110 can be applied. As described herein, rays 11, 12 and 14 are subsets of rays 9 including additional specific characteristics.

Figure 12:
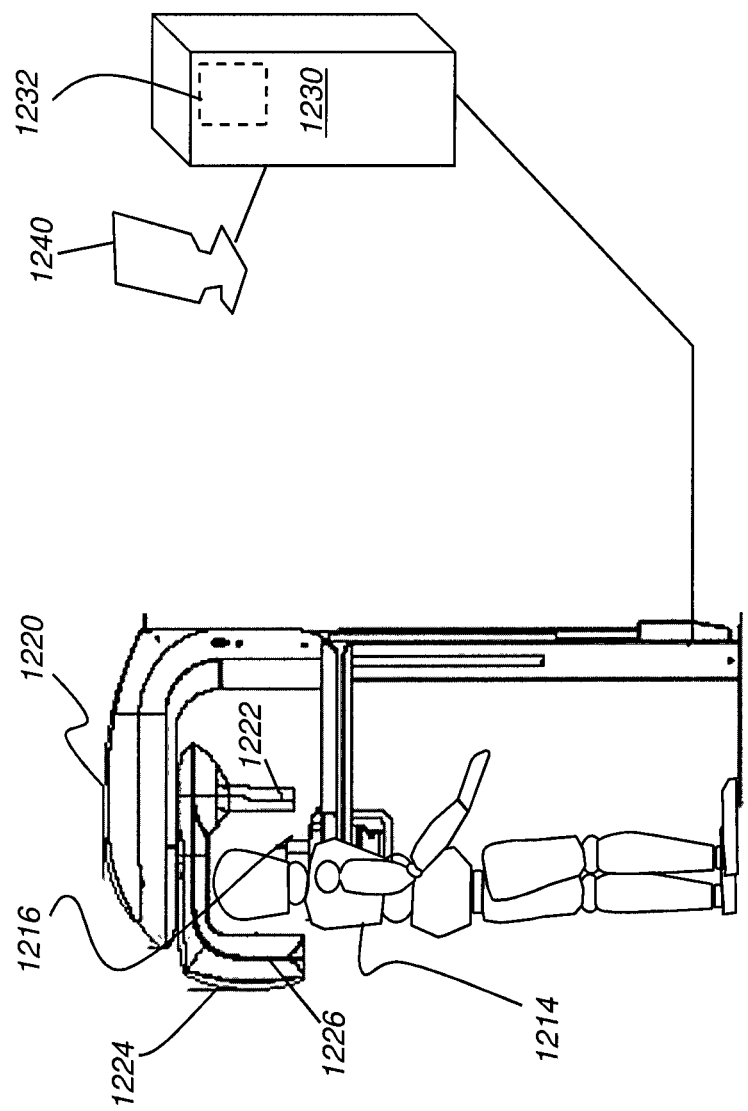
FIG. 12 is a schematic diagram that shows an imaging apparatus for CBCT imaging of an object.

FIG. 12 is a schematic diagram that shows an imaging apparatus for CBCT imaging of an object that can implement exemplary method and/or apparatus embodiments according to this application. As shown in FIG. 12, an imaging apparatus 1200 can be for acquiring, processing, and displaying a CBCT image of an object on a support or a patient 1214. A transport apparatus 1220 rotates a detector 1222 and a generator apparatus 1224 having an x-ray source 1226 at least partially about a supporting position 1216 in order to acquire multiple 2-D projection images used for 3-D volume image reconstruction. A control logic processor 1230 energizes x-ray source 1226, detector 1222, transport apparatus 1220, and other imaging apparatus in order to obtain the image content needed for 3-D imaging of the object or patient. To standardize patient 1214 position at a suitable location for imaging, stabilize head position, and to provide a reference for orbiting the detector 1222 and source 1226 about the object or patient's head with suitable geometry for imaging, supporting position 1216 can include features such as a temple support and other supporting structures. Supporting position 1216 is a location at which the object or patient's head is located; however, there may or may not be features provided at supporting position 1216 for constraining movement of the object or head during imaging. Control logic processor 1230 can include memory 1232 and is in signal communication with a display 1240 for entry of operator instructions and display of image results. The control logic processor 1230 and/or the display 1240 can be local to the imaging apparatus or remote.

Consistent with exemplary embodiments of the present application, a computer program utilizes stored instructions that perform on image data that is accessed from an electronic memory. As can be appreciated by those skilled in the image processing arts, a computer program for operating the imaging system in an exemplary embodiment of the present application can be utilized by a suitable, general-purpose computer system, such as a personal computer or workstation. However, many other types of computer systems can be used to execute the computer program of the present application, including an arrangement of networked processors, for example. The computer program for performing exemplary methods/apparatus of the present application may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing exemplary methods/apparatus of the present application may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present application may make use of various image manipulation algorithms and processes that are well known. It will be further understood that the computer program product embodiment of the present application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present application, are not specifically shown or described herein and may be selected from such algorithms, systems, hardware, components and elements known in the art.

In the description herein, exemplary embodiments of the application can be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

The invention claimed is:

1. A method for constructing a 3-D model incorporating 3-D scan image data of a maxillary dental arch positive physical model and of an opposing mandibular dental arch positive physical model, executed at least in part on data processing hardware, the method comprising:
   performing a single 3-dimensional x-ray scan of the positive physical models of the dental arches while the positive physical models of the dental arches are in an occlusal relationship to obtain 3-D image data including data representing each of the dental arch positive physical models;
   constructing respective 3-D volume models including a maxillary dental arch volume representation over a mandibular dental arch volume representation;
   generating a first 3D mesh model of surfaces of the maxillary dental arch volume representation and a second 3D mesh model of surfaces of the mandibular dental arch volume representation;
   determining contact areas where the first 3D surface mesh model and the second 3D surface mesh model intersect;
   identifying transition zones of the contact areas where the first 3D surface mesh model and the second 3D surface mesh model intersect;

clipping the contact areas using information of the transition zones to separate and close the first 3D surface mesh model and the second 3D surface mesh model; and displaying, transmitting or storing the closed first 3D surface mesh model and the closed second 3D surface mesh model.

2. The method of claim 1, further comprising segmenting teeth for each of the closed first 3D surface mesh model and the closed second 3D surface mesh model.

3. The method of claim 1, where the 3-dimensionally x-ray scanning comprises a CBCT scan.

4. The method of claim 1, where the determining contact areas comprises:
simulating a grid of rays that cross the model orthogonally to the occlusal plane;
identifying intersections of the rays with the first 3D surface mesh model and the second 3D surface mesh model; and
determining the contact areas to be where the rays do not intersect the first 3D surface mesh model and the second 3D surface mesh model.

5. The method of claim 4, where grid of rays are launched from the top of the first 3D surface mesh model or the bottom of the second 3D surface mesh model.

6. The method of claim 1, further comprising aligning the closed first 3D surface mesh model and the closed second 3D surface mesh model.

7. The method of claim 6, where the aligning comprises:
a first translation in a direction between the closed first 3D surface mesh model and closed second 3D surface mesh model until a first contact point therebetween is found;
at least one additional translation in an orthogonal direction using the first contact point as a starting point of the at least one additional translation to find other contact points and increase a total number of contact points; and
at least one rotational translation using one of the contact points as the fulcrum to find other contact points and increase the total number of contact points.

8. A method for constructing a 3-D model incorporating 3-D scan image data of a maxillary dental arch and of an opposing mandibular dental arch, executed at least in part on data processing hardware, the method comprising:
performing a single 3-dimensional x-ray scan of the physical positive models of the dental arches while the physical positive models of the dental arches are in an occlusal relationship to obtain 3-D image data including volume data representing each of the dental arch physical positive models;
constructing separate 3-D volume models including a maxillary dental arch volume representation and a mandibular dental arch volume representation aligned in an occlusal arrangement using the 3-D image data; and
displaying, transmitting or storing the 3-D model including the maxillary dental arch representation and the mandibular dental arch representation aligned in the occlusal arrangement.

9. The method of claim 8, where the 3-dimensionally x-ray scanning the physical positive models of the dental arches is performed with a thin conformal intermediary between the physical positive models of the dental arches while the physical positive models of the dental arches are in the occlusal relationship, further comprising:

generating a 3D mesh model of surfaces of each of the maxillary dental arch representation and the mandibular dental arch representation;
aligning the 3D mesh model of surfaces of the maxillary dental arch representation and the 3D mesh model of surfaces of the mandibular dental arch representation; and
displaying, transmitting or storing the aligned 3-D model including the maxillary dental arch representation aligned with the mandibular dental arch representation.

10. The method of claim 9, where the aligning comprises:
a first translation in a first direction between the maxillary dental arch representation and the mandibular dental arch representation until a first contact point therebetween is found;
at least one additional translation in a second direction orthogonal to the first direction using the first contact point as a starting point of the at least one additional translation to find other contact points and increase a total number of contact points; and
at least one rotational translation using one of the contact points as the fulcrum to find other contact points and increase the total number of contact points.

11. The method of claim 9, where the thin conformal intermediary comprises a tissue 1-5 mm thick.

12. The method of claim 8, further comprising segmenting teeth for each of the aligned 3D mesh model of surfaces of the maxillary dental arch representation and the 3D mesh model of surfaces of the mandibular dental arch representation.

13. The method of claim 8, where the 3-dimensionally x-ray scanning comprises a CBCT scan.

14. The method of claim 8, further comprising:
starting a first 3D mesh model of surfaces of the maxillary dental arch representation and a second 3D mesh model of surfaces of the mandibular dental arch representation; and
determining contact areas where the first 3D surface mesh model and the second 3D surface mesh model intersect;
identifying transition zones of the contact areas where the first 3D surface mesh model and the second 3D surface mesh model intersect;
clipping the contact areas using information of the transition zones to separate and complete the first 3D surface mesh model and the second 3D surface mesh model; and
displaying, transmitting or storing the closed first 3D surface mesh model and the closed second 3D surface mesh model.

15. A method for constructing a 3-D model incorporating 3-D scan image data of a maxillary dental arch and of an opposing mandibular dental arch, executed at least in part on data processing hardware, the method comprising:
performing a single 3-dimensional x-ray scan of the physical positive models of the dental arches while the physical positive models of the dental arches are in an occlusal relationship with a thin conformal intermediary between the physical positive models of the dental arches to obtain 3-D image data including volume data representing each of the dental arch physical positive models;
constructing separate 3-D volume models including a maxillary dental arch volume representation and a mandibular dental arch volume representation aligned in an occlusal arrangement using the 3-D image data;
generating a first 3D mesh model of surfaces of the maxillary dental arch volume representation and a second 3D mesh model of surfaces of the mandibular dental arch volume representation;
and
displaying, transmitting or storing the 3-D volume model including the maxillary dental arch volume representation and the mandibular dental arch volume representation, the first 3D surface mesh model, or the second 3D surface mesh model.

* * * * *